(12) United States Patent
Bliss et al.

(10) Patent No.: US 10,932,930 B2
(45) Date of Patent: Mar. 2, 2021

(54) ENDOLUMINAL DEVICE RETRIEVAL DEVICES AND RELATED SYSTEMS AND METHODS

(71) Applicant: W. L. Gore & Associates, Inc., Newark, DE (US)

(72) Inventors: Cody L. Bliss, Flagstaff, AZ (US); Edward H. Cully, Flagstaff, AZ (US); Jeffrey B. Duncan, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 270 days.

(21) Appl. No.: 15/982,761

(22) Filed: May 17, 2018

(65) Prior Publication Data

US 2018/0263802 A1 Sep. 20, 2018

Related U.S. Application Data

(63) Continuation of application No. 13/653,267, filed on Oct. 16, 2012, now Pat. No. 10,010,437.

(Continued)

(51) Int. Cl.
*A61F 2/962* (2013.01)
*A61B 17/221* (2006.01)
(Continued)

(52) U.S. Cl.
CPC ............ *A61F 2/962* (2013.01); *A61B 17/221* (2013.01); *A61F 2/01* (2013.01); *A61B 17/22031* (2013.01);
(Continued)

(58) Field of Classification Search
CPC ... A61B 17/22031; A61B 17/221; A61F 2/95; A61F 2/962; A61F 2/97; A61F 2/966;
(Continued)

(56) References Cited

U.S. PATENT DOCUMENTS

| 4,471,777 A | 9/1984 | McCorkle |
| 4,873,978 A | 10/1989 | Ginsburg |

(Continued)

FOREIGN PATENT DOCUMENTS

| GB | 2200848 | 8/1988 |
| JP | 2007-319271 | 12/2007 |

(Continued)

OTHER PUBLICATIONS

International Search Report and Written Opinion from PCT/2012/060510, dated Mar. 11, 2013, 17 pages.

*Primary Examiner* — Richard G Louis

(57) ABSTRACT

A retrieval device includes an elongate element having a collapsible retriever at its distal end, wherein the collapsible retriever can be axially delivered over or through an introducer to the site of an object to be retrieved, e.g., a failed endoluminal device. When the retrieval device reaches the failed endoluminal device, the endoluminal device and the retrieval device are withdrawn together through the introducer. The introducer is configured to force the retrieval device down over the endoluminal device reducing the french size of the spent endoluminal device upon extraction. The collapsible retriever can be configured to side-mount a delivery element, or it can be integrated into a delivery system.

24 Claims, 17 Drawing Sheets

Related U.S. Application Data

(60) Provisional application No. 61/548,143, filed on Oct. 17, 2011.

(51) Int. Cl.
*A61F 2/01* (2006.01)
*A61B 17/22* (2006.01)

(52) U.S. Cl.
CPC ............... *A61B 2017/2215* (2013.01); *A61B 2017/22035* (2013.01)

(58) Field of Classification Search
CPC .. A61F 2/9665; A61F 2/01; A61F 2002/9528; A61F 2002/016; A61F 2002/011
USPC ...................................................... 606/200
See application file for complete search history.

(56) References Cited

U.S. PATENT DOCUMENTS

| | | | |
|---|---|---|---|
| 4,990,151 A | 2/1991 | Wallsten | |
| 5,002,556 A | 3/1991 | Ishida | |
| 5,102,415 A | 4/1992 | Guenther et al. | |
| 5,176,687 A | 1/1993 | Hasson et al. | |
| 5,190,561 A | 3/1993 | Graber | |
| 5,259,366 A * | 11/1993 | Reydel | A61B 1/00135 383/203 |
| 5,312,417 A | 5/1994 | Wilk | |
| 5,370,647 A | 12/1994 | Graber | |
| 5,417,697 A | 5/1995 | Wilk | |
| 5,464,408 A | 11/1995 | Duc | |
| 5,509,923 A | 4/1996 | Middleman | |
| 5,632,746 A | 5/1997 | Middleman | |
| 5,643,282 A | 7/1997 | Kieturakis | |
| 5,681,347 A | 10/1997 | Cathcart | |
| 5,707,359 A | 1/1998 | Bufalini | |
| 5,749,879 A | 5/1998 | Middleman | |
| 5,836,953 A | 11/1998 | Yoon | |
| 5,836,969 A | 11/1998 | Kim | |
| 5,904,690 A | 5/1999 | Middleman | |
| 5,924,175 A | 7/1999 | Lippitt | |
| 5,947,995 A * | 9/1999 | Samuels | A61B 17/22032 606/200 |
| 6,007,558 A | 12/1999 | Ravenscroft et al. | |
| 6,027,508 A | 2/2000 | Ren | |
| 6,126,673 A | 10/2000 | Kim | |
| 6,156,055 A | 12/2000 | Ravenscroft | |
| 6,159,230 A | 12/2000 | Samuels | |
| 6,187,016 B1 | 2/2001 | Hedges | |
| 6,231,581 B1 | 5/2001 | Shank et al. | |
| 6,306,141 B1 | 10/2001 | Jervis | |
| 6,383,195 B1 | 5/2002 | Richard | |
| 6,468,290 B1 | 10/2002 | Weldon | |
| 6,726,621 B2 | 4/2004 | Suon | |
| 6,802,846 B2 | 10/2004 | Hauschild | |
| 6,971,988 B2 | 12/2005 | Orban | |
| 7,041,117 B2 | 5/2006 | Suon | |
| 7,063,707 B2 | 6/2006 | Bose | |
| 7,179,275 B2 | 2/2007 | McGuckin | |
| 7,338,512 B2 | 3/2008 | McGuckin | |
| 7,537,601 B2 | 5/2009 | Cano et al. | |
| 7,658,747 B2 | 2/2010 | Forde | |
| 7,837,692 B2 | 11/2010 | Mulholland | |
| 7,914,540 B2 | 3/2011 | Schwartz | |
| 7,993,362 B2 | 8/2011 | Lowe | |
| 8,025,668 B2 | 9/2011 | McCartney | |
| 8,038,704 B2 | 10/2011 | Sherburne | |
| 8,043,208 B2 | 10/2011 | Windheuser | |
| 8,109,940 B2 | 2/2012 | McGuckin | |
| 8,118,829 B2 | 2/2012 | Carrison | |
| 2002/0002383 A1 | 1/2002 | Sepetka et al. | |
| 2002/0183781 A1* | 12/2002 | Casey | A61B 17/22031 606/198 |
| 2004/0073243 A1 | 4/2004 | Sepetka et al. | |
| 2005/0137620 A1 | 6/2005 | Alkhatib | |
| 2006/0136043 A1 | 6/2006 | Cully et al. | |
| 2007/0135820 A1 | 6/2007 | Que et al. | |
| 2008/0161640 A1 | 7/2008 | Weisman | |
| 2008/0312681 A1 | 12/2008 | Ansel et al. | |
| 2009/0222035 A1 | 9/2009 | Schneiderman | |
| 2009/0240238 A1 | 9/2009 | Grodrian et al. | |
| 2010/0016792 A1 | 1/2010 | Hirszowicz | |
| 2010/0042107 A1 | 2/2010 | Merrifield | |
| 2010/0137892 A1 | 6/2010 | Krolik et al. | |
| 2010/0234876 A1 | 9/2010 | Watson | |
| 2011/0251682 A1 | 10/2011 | Murray, III et al. | |
| 2013/0018387 A1 | 1/2013 | Diamant | |
| 2014/0088634 A1* | 3/2014 | Sanati | A61F 2/013 606/200 |

FOREIGN PATENT DOCUMENTS

| | | |
|---|---|---|
| JP | 2007319271 A | 12/2007 |
| JP | 2008-229354 | 10/2008 |
| JP | 2009-523496 | 6/2009 |
| JP | 2009-542302 | 12/2009 |
| JP | 4917176 B1 | 4/2012 |
| WO | WO-2000056231 | 9/2000 |
| WO | WO-2000056231 A1 | 9/2000 |
| WO | WO-2001035831 A1 | 5/2001 |
| WO | WO-2007084431 A2 | 7/2007 |
| WO | WO-20070084431 A2 | 7/2007 |
| WO | WO-2008004238 | 1/2008 |
| WO | WO-2008004238 A2 | 1/2008 |
| WO | WO-2010034021 A2 | 3/2010 |
| WO | WO-2010034021 | 9/2010 |
| WO | WO-2011110356 A1 | 9/2011 |
| WO | WO-2013059247 A1 | 4/2013 |
| WO | WO-2009011721 A1 | 1/2019 |

* cited by examiner

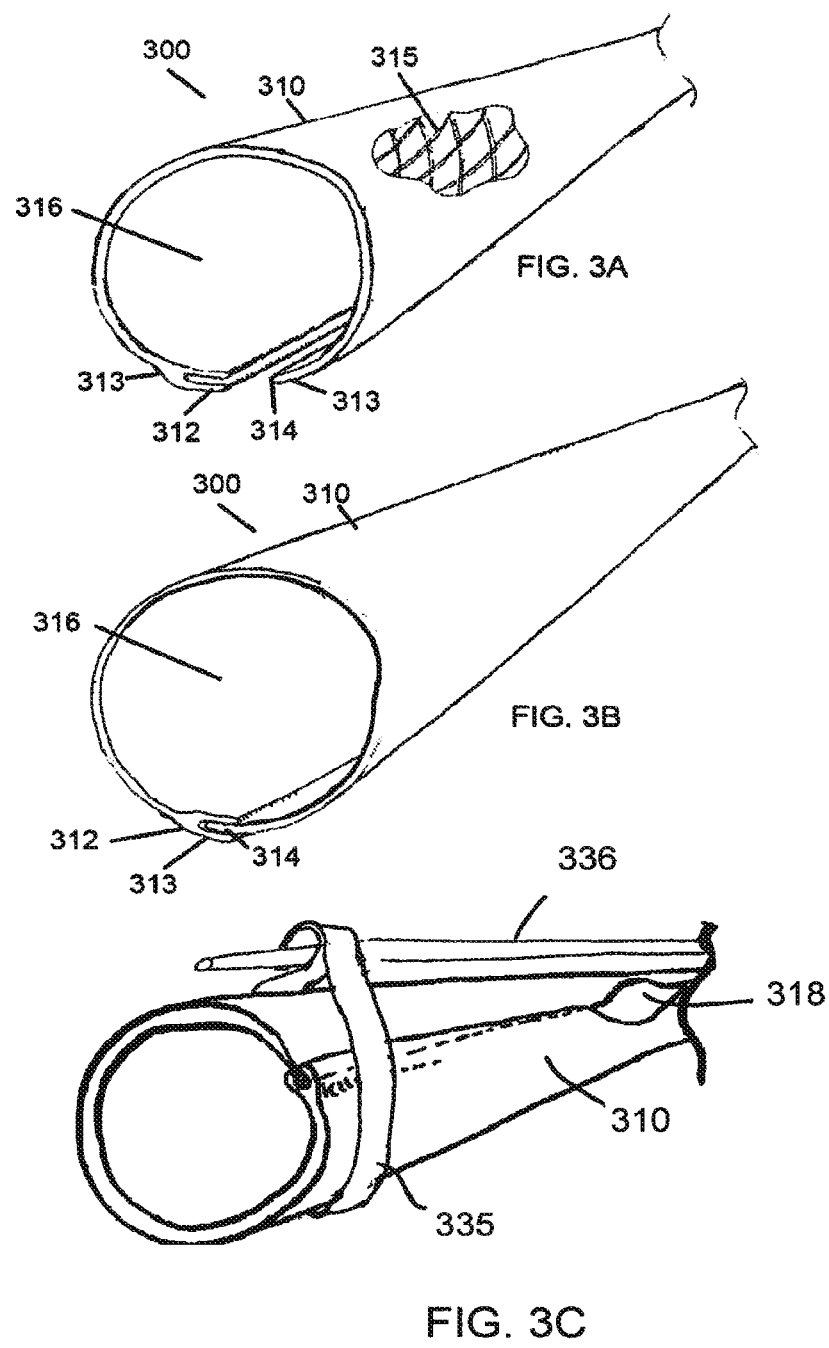

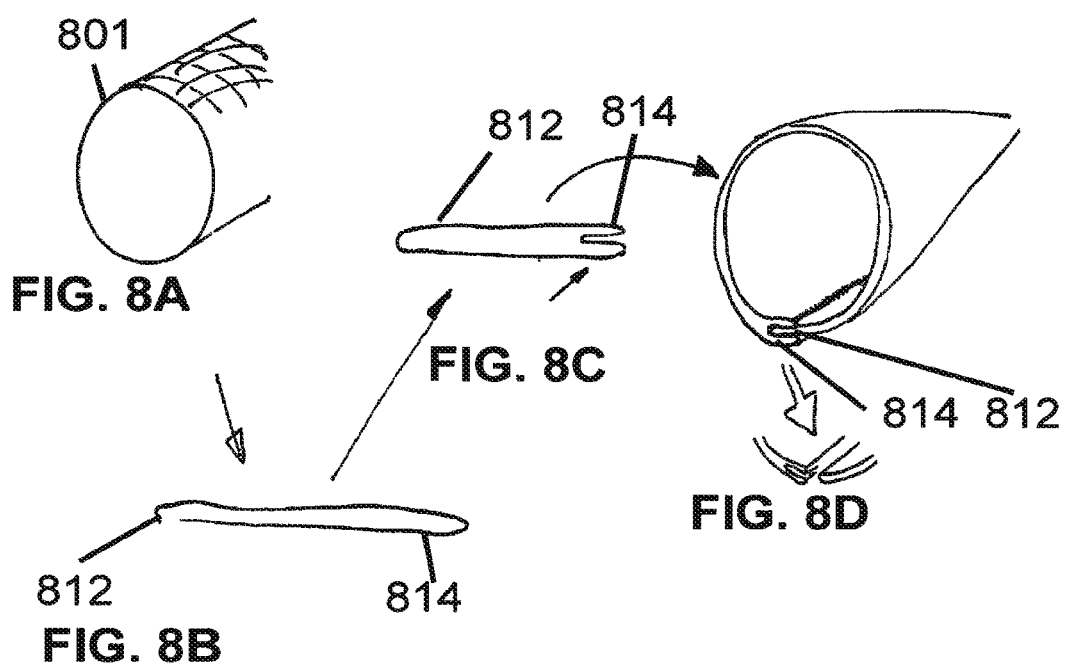

ENDOLUMINAL DEVICE RETRIEVAL DEVICES AND RELATED SYSTEMS AND METHODS

CROSS-REFERENCE TO RELATED APPLICATION

This application is a continuation of U.S. patent application Ser. No. 13/653,267, filed Oct. 16, 2012, entitled "ENDOLUMINAL DEVICE RETRIEVAL DEVICES AND RELATED SYSTEMS AND METHODS", which claims the benefit of U.S. Provisional Application No. 61/548,143 filed on Oct. 17, 2011, entitled "ENDOLUMINAL DEVICE RETRIEVAL DEVICES AND RELATED SYSTEMS AND METHODS", both of which are hereby incorporated by reference in their entireties.

BACKGROUND OF THE DISCLOSURE

Field of the Disclosure

The disclosure relates to devices to retrieve safely and effectively an object, such as an endoluminal device, from the vasculature.

Discussion of the Related Art

Endoluminal devices can fail prior to removing through the accompanying introducer sheath. For example, endoluminal balloons can rupture, become snagged on plaque and/or simply fail to "repack" prior to removing. Such failures can be detrimental to the procedure, the anatomy, and the patient, and can even require a costly surgical bailout.

There is thus a need for devices to safely and effectively retrieve endoluminal devices from the vasculature, especially damaged endoluminal balloons.

SUMMARY OF THE DISCLOSURE

Retrieval devices and related systems and methods are provided. An embodiment of a retrieval device comprises an elongate element having a collapsible retriever at its distal end, wherein the collapsible retriever can be axially delivered over or through an introducer to the site of an object to be withdrawn, e.g., a failed endoluminal device. When the retrieval device reaches the object to be withdrawn, the object 106 and the retrieval device are retracted together through the introducer. The introducer is configured to force the retrieval device down over the object reducing the french size (i.e., crossing profile) of the object upon extraction.

In various embodiments, the retrieval device can be side mounted onto a delivery element, such as a guidewire or catheter. The retrieval device can have an inverted feature along its length, a discontinuous section along its length, or an interlocking/interfacing section along its length to facilitate side mounting. In an embodiment, the collapsible retriever as described herein can have a coupled and uncoupled configuration that permits side mounting onto a delivery element. Optionally, the retrieval device can elongate and collapse as it is retracted into the introducer. Other embodiments comprise methods of making and using the same.

BRIEF DESCRIPTION OF THE DRAWINGS

The accompanying drawings are included to provide a further understanding of the disclosure and are incorporated in and constitute a part of this specification, illustrate embodiments of the disclosure, and together with the description serve to explain the principles of the disclosure.

FIGS. 3A to 3B illustrate an embodiment of the collapsible retriever having an interlocking mechanism in an uncoupled configuration and a coupled configuration, respectively;

FIG. 3C illustrates an embodiment of the collapsible retriever having an interlocking mechanism in a coupled configuration having a circumferential member to compress the distal end and an aperture at the proximal base;

FIGS. 8A to 8D illustrate a method for making an embodiment as shown in FIGS. 3A to 3C.

DETAILED DESCRIPTION OF THE ILLUSTRATED EMBODIMENTS

Figure 1:
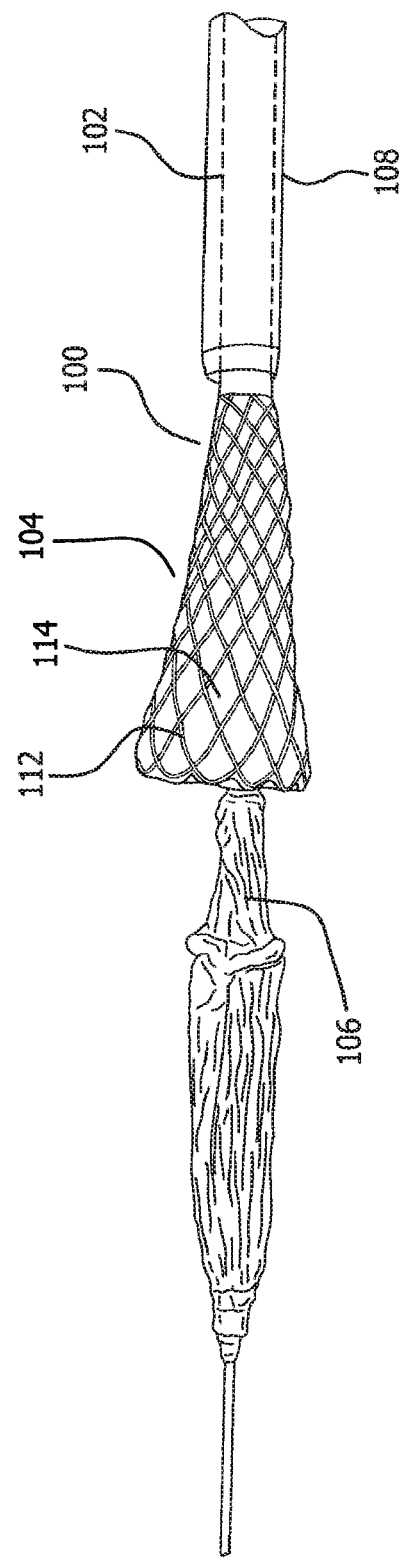
FIG. 1 illustrates an embodiment of a retrieval device shown with the balloon portion of a balloon catheter and an introducer sheath.

Persons skilled in the art will readily appreciate that various aspects of the present disclosure can be realized by any number of methods and apparatuses configured to perform the intended functions. Stated differently, other methods and apparatuses can be incorporated herein to perform the intended functions. It should also be noted that the accompanying drawing figures referred to herein are not all drawn to scale, but can be exaggerated to illustrate various aspects of the present disclosure, and in that regard, the drawing figures should not be construed as limiting. Finally, although the present disclosure can be described in connection with various principles and beliefs, the present disclosure should not be bound by theory.

The terms "proximal" and "distal," when used herein in relation to a device or device component, refer respectively, to directions closer to and farther away from the device's operator. Since the present disclosure is not limited to peripheral or central approaches, the device should not be narrowly construed when using the terms proximal or distal since device features can be slightly altered relative to the anatomical features and the device position relative thereto.

As used herein, the term "elongate element" includes any longitudinally extending structure with or without a lumen there through. Thus, elongate elements include but are not limited to tubes with lumens (e.g., catheters), solid rods, hollow or solid wires (e.g., guidewires), hollow or solid stylets, metal tubes (e.g., hypotubes), polymer tubes, fibers, and filaments. Elongate element can comprise various additional features or properties to enhance its function, such as electrical conductors, radiopaque elements, radioactive elements, echogenic elements, and radiographic elements.

Elongate elements can be any material and can have any cross-sectional shape including, but not limited to, profiles that are circular, ovoidal, polygonal, or random.

According to one aspect of an embodiment, devices to safely and effectively retrieve an object, e.g., endoluminal devices, thrombus, or other undesired matter, from the vasculature are provided. As used herein, "endoluminal device" means any device configured for use in the vasculature (e.g., balloons, stents, stent grafts, valves, etc.), and "vasculature" includes arterial and venous vessels, as well as other anatomical lumens and cavities not in direct communication with the cardiovascular system (e.g., arteries, veins, bronchi, etc.).

An embodiment of a retrieval device comprises a collapsible retriever (e.g., a collapsible funnel) that can be side mounted over a delivery element to the site of an object to be retrieved, e.g., a failed endoluminal device. The collapsible retriever can have a discontinuous section or inverted section to facilitate side-mounting. Similarly, the collapsible retriever can comprise an interlocking or interfacing mechanism which permits the retriever to open along its length in order to be side mounted onto delivery element and then closed to then be advanced along the length of the delivery element. When the retrieval device reaches the object, the object and the retrieval device are withdrawn together through a concentric coaxial element, e.g., the introducer. The introducer can be configured to force the retrieval device down over the object reducing the french size of the object upon retraction. In this regard, endoluminal access remains uncompromised and the procedure can continue as planned.

According to another aspect of an embodiment, a retrieval device is provided comprising a collapsible retriever at the distal end of an elongate element. In embodiments, a distal end of the elongate element is coupled with a proximal end of the collapsible retriever. In such embodiments, the coupling can be permanent or temporary. In other embodiments, the elongate element and the collapsible retriever are integral, for example, comprising a common support frame and/or formed on a common mandrel from a common material. Notwithstanding the above, it is contemplated that the collapsible retriever can also be mounted on any section of an elongate member, e.g., an intermediate section.

Relative axial movement between an elongate element and a delivery element can be accomplished with various structural relationships and configurations. For example, in various embodiments, an elongate element comprises a lumen extending therethrough having an inner diameter greater than the outer diameter of at least a portion of an endoluminal device delivery element. In such embodiments, the retrieval device is concentrically deliverable over the endoluminal device delivery element. In other embodiments, an elongate element comprises a loop at its distal end having an inner diameter greater than the outer diameter of at least a portion of an endoluminal device delivery element. In such embodiments, the retrieval device is slideably deliverable over the endoluminal device delivery element via the loop of the elongate element.

Collapsible retriever is generally any device configured to envelop at least partially an object, e.g., a catheter-based endoluminal device such as a damaged endoluminal balloon and then sufficiently flexible to allow a coaxial delivery element to force the retriever down into a collapsed configuration. Collapsible retriever can partially or completely envelop or engulf an object so that a cumulative force can be exerted and distributed substantially evenly about at least a portion of the object. Stated differently, collapsible retriever can be configured not to pull in one spot of an object, e.g., as a snare, which can break the targeted device, e.g., where an implantable cardioverter defibrillator or the like has become brittle. An embodiment of collapsible retriever can have any number of shapes when in the coupled configuration, for example, a generally tapered, funnel, frustoconical, conical, and/or trumpet to form tapered lumen. Other shapes include a cylindrical or prismoidal shape.

In an embodiment, optionally, the collapsible retriever can be configured to adjust to an object having a larger dimension than the distal mouth of the retriever. In an embodiment, upon the application of a compressive force applied along an axis formed between the proximal end and the distal end of the retriever, the cross-sectional area of the retriever, at least at the distal end, can increase. Thus, during use, when the retriever encounters an object to be retrieved, that may have an outer dimension larger than the outer dimension of the retriever, the retriever presses against the object, causing a compressive force to be applied on the distal rim of the retriever, and thereby causing an enlargement of the distal mouth of the retriever. For example, the wall of the retriever can comprise a lattice element defining the tapered lumen and configured to radially expand upon the application of a compressive force applied along the axis formed between the proximal end and the distal end. Lattice element includes lattice constructs but also includes braided elements, longitudinally looped elements, or any other structural or material configuration, which will facilitate the partial enveloping of the object through widening of the mouth. The lattice element can facilitate an increase in cross-sectional area of about 100% or more. For example, a diameter of a conical collapsible retriever at the distal end can increase from 20 mm to 30 mm. In another embodiment, the collapsible retriever can comprise at least one split, break, or otherwise discontinuous section in the retriever material at its distal rim that allows for an increase in the cross-sectional area at the mouth of the retriever. The split can run generally perpendicular to the cross-sectional plane of the retriever or be diagonal thereto. In an embodiment, the interlocking mechanism can be configured to uncouple at the distal end to form a split in order to facilitate an increase in the cross-sectional area. In a further embodiment, as the collapsible retriever is retracted into the coaxial element, the interlocking mechanism can re-couple.

The collapsible retriever can also comprise one or more structural support elements. The lattice element described above can also be a structural support element. The support element allows for the retriever to have a collapsed configuration and an expanded or open configuration. Thus, the retriever can pass through the lumen of a coaxial delivery element (e.g., an introducer sheath), but then can self-expand or be expanded once it exits the distal end of the delivery element. Optionally, the support element can also provide some column strength to the retriever to facilitate capture of the object. In an embodiment, the support element can comprise wires, struts, braids, lattices, wires or ring or helical stent elements, any of the foregoing either laser cut from a tube or formed separately. To facilitate self-expansion, the structural support elements can comprise a shape-memory material, such as nitinol. The structural support elements can be heat set in an open (radially expanded) position or a closed (radially collapsed) position, the latter to reduce its size while in the anatomy. In other embodiments, however, the structural support elements can be comprised of other materials, self-expandable or otherwise expandable (e.g., with a fluid-filled balloon), such as various metals (e.g., stainless steel), alloys and polymers.

The collapsible retrievers can further comprise various materials attached to said structural support elements, including, but not limited to, polymers, such as fluoropolymers like an expanded polytetrafluoroethylene ("ePTFE"), a highly densified ePTFE, a high strength toughened fluoropolymer, polyamides, polycarbonates, polyolefins (such as polypropylenes and polyethelyenes), and the like. Such materials can take the form of, inter alia, meshes, films, fabrics, covers and the like. In an embodiment, to facilitate withdrawal of the object or mitigate undesired release of emboli/particles that may break away from the object, the collapsible retriever can be overlaid with a film.

In an embodiment, optionally, the collapsible retriever, having an interior surface and an exterior surface, can comprise a lubricious coating or material having a low surface energy/friction on the exterior surface, which can facilitate retraction of collapsible retriever and the object into the lumen of a coaxial delivery element, such as an introducer sheath or a catheter. In addition, to facilitate capture of the object, the interior surface of retriever at least at the distal section (up to its entirety) can have a lubricous coating, which enables the widening mouth to slip around the device. On the other hand, the interior surface at least at a proximal section (up to its entirety) of collapsible retriever can be rough or tacky, e.g., to apply a gripping force to the object being retrieved yet provide the exterior surface(s) as smooth or lubricious to slideably interact with the internal surface(s) of its catheter/sheath actuator. Similarly, the collapsible retriever can comprise one or more hooks or barbs at a distal and/or on the interior surface thereof. A hook or barb can serve to grasp or perforate an object.

In various embodiments, a collapsible retriever can have a radially collapsed delivery/removal configuration and a radially expanded enveloping configuration. A collapsible retriever can further be configured to be self-expanding or have one or more self-expanding structural support elements. A collapsible retriever can further be configured to be self-expanding or have one or more self-expanding structural support elements. As such, to facilitate delivery, in various embodiments, the collapsible retriever and/or a portion thereof can be restrained, compressed or otherwise held in a radially collapsed delivery/removal configuration by a surrounding constraining element until it is deployed therefrom by relative axial movement of the collapsible retriever and the surrounding constraining element. In other embodiments, the collapsible retriever and/or a portion thereof is restrained or otherwise held in a radially collapsed delivery configuration by a releasable or removable cover such as a sleeve, sheath, sock or other constraining device. In an embodiment, a constraining sheath can comprise a slit that facilitates the retriever to be side-mounted. In other embodiments, the constraining sheath can be configured to slide away from retriever as the retriever is being inserted into the coaxial delivery element.

In other embodiments, a split "cheater" can be utilized to assist in the collapse and guidance of the collapsible retriever into a hemostasis valve. The split "cheater" can be snapped onto the catheter. The collapsible retriever can then be snapped on to the catheter, in a manner, which allows the collapsible retriever to be back-loaded into the cheater. For example, an elongate member can be snapped into the cheater and the collapsible retriever can be distal to the cheater. The retriever tool can be pulled into the cheater and then all components can be pushed through the hemostasis valve. In this manner, the collapsible retriever can be transferred from the cheater to a coaxial element (e.g., an introducer sheath) about a delivery element.

In an embodiment, the collapsible retriever can be configured to elongate during retraction to further envelope the endoluminal device. For example, the collapsible retriever can comprise a frame at its distal end, which is forced to pivot and extend in a distal direction in order to collapse and retract into a coaxial delivery device, such as an introducer sheath.

Embodiments can be steerable. For example, the elongate element and/or the collapsible retriever can be housed in a sheath, sock or other constraining device. Such a constraining device can have a deployment line which, if locked (e.g., pin, wire or other), acts as a tension line to cause bending of the elongate element and/or the collapsible retriever.

Optionally, in some embodiments, a collapsible retriever can comprise a plurality of pleats along its length. Such pleats can facilitate re-pleating a pleated balloon.

Optionally, in some embodiments, a collapsible retriever can comprise a circumferential element about the collapsible retriever, e.g., at a site in the distal section, configured to radially compress the portion of the retriever about which it is located. The circumferential member can be a filament, thread, ribbon, or the like. In an embodiment, the circumferential member can be woven through the lattice element. The circumferential member can be integral with or coupled to an axial member, which can either be axially moved or rotated. Upon axial displacement or rotation of the axial member, the diameter of the circumferential member is reduced, facilitating radial compression of the retriever.

Elongate elements and/or collapsible retrievers can comprise a therapeutic agent, for example, be coated or imbibed with a therapeutic agent, whether dry, gel or liquid. Examples of therapeutic agents comprise antiproliferative/antimitotic agents including natural products such as *vinca* alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP)IIbIIIa inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine{cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF) platelet derived growth factor (PDGF), erythropoietin; angiotensin receptor blocker; nitric oxide donors; anti-sense oligionucleotides and combinations thereof; cell cycle inhibitors, mTOR inhibitors, growth factor signal transduction kinase inhibitors, chemical compound, biological molecule, nucleic acids such as DNA and RNA, amino acids, peptide, protein or combinations thereof.

Any portion of an elongate element and/or a collapsible retriever can comprise a radio-opaque or echogenic element that enhances imaging or detection during and/or following delivery or deployment. Radio-opaque markers can be comprised of one or more of tungsten, gold, platinum and the like.

By way of non-limiting examples for retrieving endoluminal balloons, and with reference now to the FIGS., illustrated in FIG. 1 is a retrieval device 100 shown with the balloon portion of a balloon catheter 106 and an introducer sheath 108. In this illustrated embodiment, retrieval device 100 comprises an elongate element 102 having a collapsible retriever 104 at a distal end of elongate element 102.

As shown, elongate element 102 and collapsible retriever 104 comprise a common lumen extending therethrough having an inner diameter greater than the outer diameter of the catheter portion of balloon catheter 106. Collapsible retriever 104 is formed from a shape-memory lattice structural support element 112 supporting a film 114 of an ePTFE. In this illustrated embodiment, the inner diameter of the distal portion of collapsible retriever 104 is sized to accommodate the balloon portion of balloon catheter 106. The inner diameter of the distal portion of elongate element 102 is sized to accommodate the catheter portion of balloon catheter 106. Retrieval device 100 is thus concentrically deliverable over balloon catheter 106.

With the balloon portion of balloon catheter 106 safely within collapsible retriever 104, lattice structural support element 112 (and in turn, collapsible retriever 104 and its contents) can be radially collapsed by relative axial movement with introducer sheath 108. Specifically, axial movement causes lattice structural support element 112 to contact the distal end of introducer sheath 108. Because introducer sheath 108 exhibits greater rigidity than collapsible retriever 104 does, it is radially collapsed.

Figure 2A:
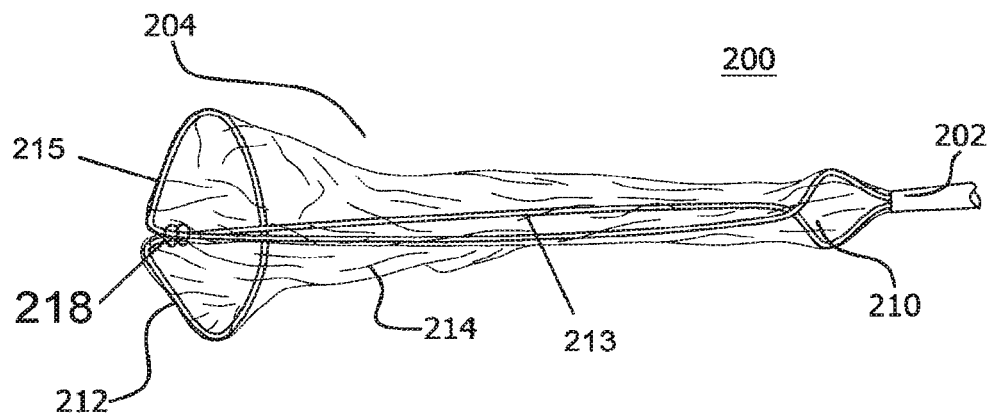
FIG. 2A illustrates another embodiment of a retrieval device.
Figure 2B:
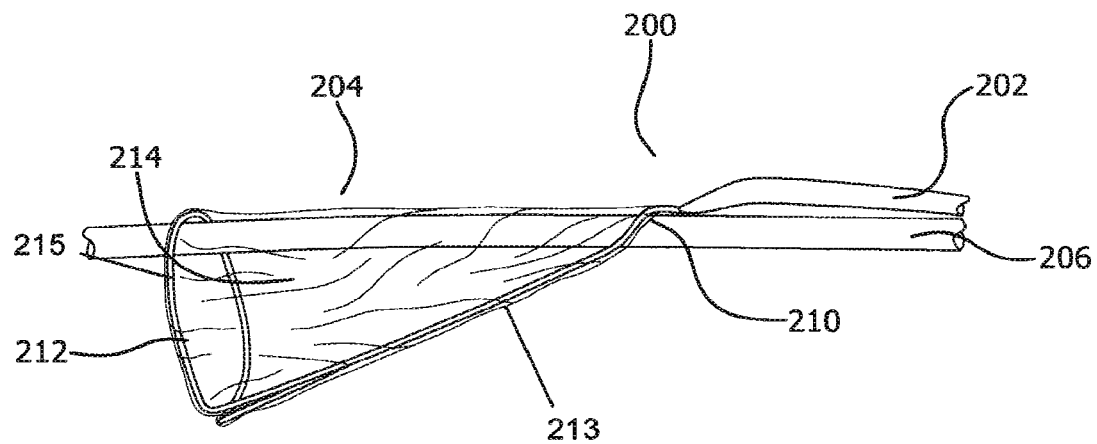
FIG. 2B illustrates the embodiment of the retrieval device of FIG. 2A with the central portion of a balloon catheter.

FIG. 2A illustrates another retrieval device 200. FIG. 2B shows retrieval device 200 with the catheter portion of a balloon catheter 206. In this illustrated embodiment, retrieval device 200 comprises an elongate element 202 having a collapsible retriever 204 at a distal end of elongate element 202. The collapsible retriever 204 can be slideably delivered over an endoluminal device delivery element.

In various embodiments, retrieval device 200 can comprise elongate element 202 having a proximal end and a distal end and a longitudinal axis. Collapsible retriever 204 can be located at the distal end of elongate element 202. Collapsible retriever 204 can comprise a proximal end and a distal end and can at least partially define a lumen there through. Collapsible retriever 204 can be configured to extend in a proximal to distal direction and collapse about at least a portion of an endoluminal device upon retracing into at least one of a catheter and an introducer sheath.

In various embodiments, collapsible retriever 204 comprises a pivotable frame 215 at its distal end. Pivotable frame 215 can at least partially define the lumen of collapsible retriever 204 at its distal end. During use, specifically during retraction into the lumen of an introducer or the like, pivotable frame 215 can pivot from a first position, which is generally transverse to the longitudinal axis of the elongate element, to a second position, which is more aligned with the longitudinal axis than the first position. Pivotable frame 215 pivots in a proximal to distal direction and elongates when transitioning from the first position to the second position. As it continues to be retracted into the lumen, pivotable frame 215 collapses about the endoluminal device. In this manner, collapsible retriever 204 can elongate and further envelope an endoluminal device.

Pivotable frame 215 comprises a material with sufficient rigidity to maintain the frame construct but sufficiently flexible to be collapsible. Pivotable frame 215 can be formed from structural support element 212. In an embodiment, pivotable frame 215 can comprise a shape-memory material; specifically, pivotable frame 215 can comprise a nitinol wire. Other suitable materials can include any other biocompatible materials with the properties as described above, including shape memory polymer or other ductile metals.

As shown, collapsible retriever 204 can also comprise a loop 210 at its proximal end having an inner diameter greater than the outer diameter of the catheter portion of balloon catheter 206. In an embodiment, loop 210 can be formed from structural support element 212. Loop 210 can comprise a closed-loop configuration or an open-loop configuration. An open-loop configuration permits retrieval device 200 to be loaded onto the catheter portion of balloon catheter 206 from the side, i.e., side mounted, rather than threading over a distal end of balloon catheter 206. This "side mountable" configuration can be beneficial in that the hub of the endoluminal device being retrieved can be retained (not cut off).

An open-loop configuration can form an incomplete circle or can overlap with itself creating a split loop or over-wound loop or a hybrid of the two. In this illustrated embodiment of an open-loop configuration, the inner diameter of the distal portion of collapsible retriever 204 is sized to accommodate the balloon portion of balloon catheter 206. The inner diameter of loop 210 is sized to accommodate the catheter portion of balloon catheter 206. Retrieval device 200 is thus slideably deliverable over balloon catheter 206 via loop 210 of collapsible retriever 204. The open-loop configuration facilitates the device being side mountable.

In various embodiments, structural support element 212 comprises at least one support arm 213 that extends from a proximal end to a distal end of collapsible retriever 204 and away from loop 210. Support arm 213 can be coupled, indirectly or directly, to pivotable frame 215. In an embodiment, support element comprises two arms 213, which can connect and form pivotable frame 215 at the distal portion of collapsible retriever 204. This structure allows collapsible retriever 204 to wind about the balloon portion of balloon catheter 206 and longitudinally extend to envelope an additional portion of the balloon portion as it is retracted. Similar to pivotable frame 215, support arm 213 can comprise a shape memory material.

In an embodiment, structural support element(s) 212, particularly pivotable frame 215 and support arm(s) 213, supports a flexible, preferably thin material or mesh to form a wall 214 of collapsible retriever 204. Wall 214 at least partially defines the lumen of the collapsible retriever. In various embodiments, wall 214 can comprise a discontinuous section along its length to enable device 200 side-mountable, similar to the open-loop configuration of loop 210 described above. In an embodiment, two support arms 213 can define the boundaries of this discontinuous section. In other embodiments, pivotable frame 215 can be over-wound such that a portion of wall 214 interfaces with itself in between two support arms 213.

Because pivotable frame pivots in a distal direction during retraction, flexible material must yield without tearing when the pivotable frame pivots. In an embodiment, wall 214 can comprise some slack (or extra length) in the flexible material on the portion that would otherwise undergo tension during use. Alternatively, the flexible material can comprise an elastomeric material or any other material or construct that can yield to the expected amount of tension and not tear. The flexible material can comprise a mesh, film, fabric, and the like. For example, the flexible material can comprise an ePTFE film.

Collapsible retriever 204 can comprise any shape as previously described. In embodiment, collapsible retriever 204 comprises a tapered lumen such that a cross-sectional area at the distal end is greater than a cross-sectional area at the proximal end. In other embodiments, collapsible retriever can define a generally cylindrical or other prismoidal lumen.

With the above described embodiment, once the balloon portion of balloon catheter 206 safely within collapsible retriever 204, wire structural support element 212 (and in turn, collapsible retriever 204 and its contents) can be collapsed by relative axial movement with a surrounding coaxial delivery element (e.g., an introducer sheath or a catheter, among other components). Specifically, axial movement causes structural support element 212 to retract and to contact the distal end of the surrounding coaxial element. Because the surrounding coaxial element exhibits greater rigidity than collapsible retriever 204 does, collapsible retriever 204 can be elongated and collapsed.

Optionally, collapsible retriever 204 can comprise an interlocking mechanism. Support arms 213 can be configured to fixedly engage each other. In an embodiment, with reference to FIG. 2A, a suture 218 or the like can be used to join the arms together. In another embodiment, support arm 213 can comprise an inverted section that can engage the other side, as is described below.

In accordance with the present disclosure, with reference to FIG. 3A to FIG. 3C, a retrieval device of a collapsible retriever can comprise an uncoupled configuration (as illustrated in FIG. 3A) and a coupled configured (as illustrated in FIGS. 3B and 3C). Retrieval device 300 can comprise a collapsible retriever 310 having a proximal end and a distal end, as well as a first side edge 312 and a second side edge 314. To form a coupled configuration, first side edge 312 and second side edge 314 can temporarily or permanently engage each other to form a lumen 316, e.g., a tapered lumen as shown. The tapered lumen can be dimensioned so that the delivery element can extend through the lumen.

To facilitate engagement, the two side edges 312, 314 can be interlockable or otherwise engaged to maintain contact with the two edges. Any suitable interlocking mechanism 313 can be used. With reference to FIG. 3A, interlocking mechanism 313 can comprise a ziplock or a tongue and channel groove interface. In other embodiments, interlocking mechanism 313 can comprise an interfacing section configured to temporarily or permanently engage each other, e.g., with an adhesive material on a portion of an interfacing section. Other embodiments include a hook and loop fastener (Velcro®), a hook and a catch, a button, a zipper, tie, clasp or the like. More simply, the edges may stay engaged by applying tension to the retrieval device. In addition, applying tension can cause the retrieval cone to begin to enter the mouth of the introducer or sheath. Entering the sheath can tend to force the interlocking edges together.

In an embodiment, optionally, collapsible retriever 310 can be configured to adjust to an object having a larger dimension than the distal mouth of the retriever, e.g., by way of a lattice element 315, a split, interlocking mechanism 313, or the like.

Figure 6A:
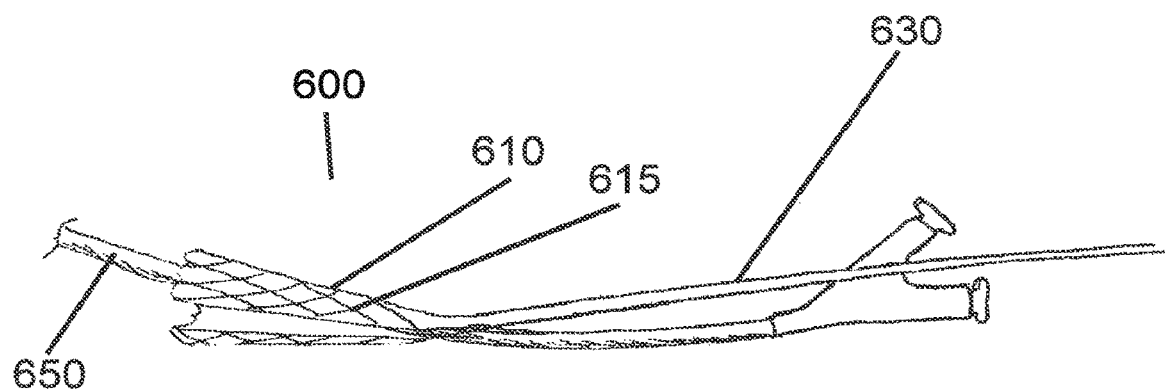
FIGS. 6A-6C progressively illustrate a method for retrieving a failed endoluminal balloon using an embodiment of the retrieval device of FIGS. 3A-3C.

In a further embodiment, with reference to FIG. 6A, retrieval device 600 can comprise collapsible retriever 610 mounted on the distal section of elongate element 630. In such embodiments, the coupling can be permanent or temporary. Elongate element 630 can be configured for relative axial movement with another elongate element, e.g., a delivery element 650 (e.g., a catheter-based endoluminal device delivery element such as a balloon catheter). In an embodiment, elongate element 630 and collapsible retriever 610 are permanently coupled, for example, comprising a common support frame and/or formed on a common mandrel from a common material, or otherwise permanently joined together.

In other embodiments, with reference to FIG. 3C, collapsible retriever 310 can be retrofitted onto an elongate member. Interlocking mechanism 313 can form an aperture 318, near the base, through which an elongate element can extend. This section can be coated with a material or otherwise configured to mitigate slipping. In other embodiments, a clamp member can be located at base of collapsible retriever 310. In an embodiment, the member can be a barrel shape with an aperture there through that permits side mounting but then clamps down on the elongate member to fix the position of collapsible retriever 310 on the elongate member.

In an embodiment, with reference to FIG. 3C, collapsible retriever 310 can further comprise a circumferential member 335, as previously described, which can radially compress the distal end. Circumferential member 335 can be controlled with an axial member 336, which can be retracted or rotated to cause radial compression.

In the case of an angioplasty balloon that has been used and will not repack well enough to re-enter the guide or introducer for egress, described embodiments could be side-mounted to the side of the balloon catheter shaft while maintaining a negative pressure inside the balloon. ("Negative pressure," as used herein, is a pressure less than the pressure of the surrounding environment.) The negative pressure, along with the funneling and re-packing effect of the present disclosure, will allow minimally invasive and more effective removal of the balloon.

Figure 4A:
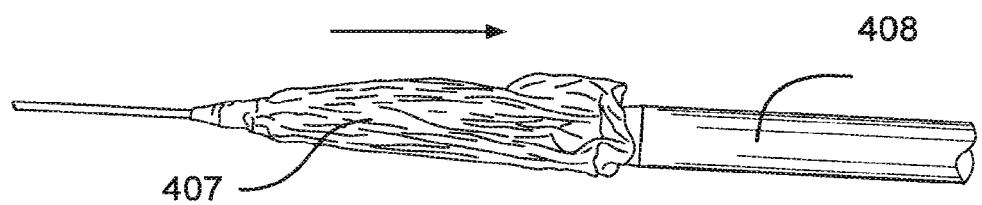
FIGS. 4A-4G progressively illustrate a method for retrieving a failed endoluminal balloon using an embodiment of the retrieval device of FIG. 1.
Figure 4B:
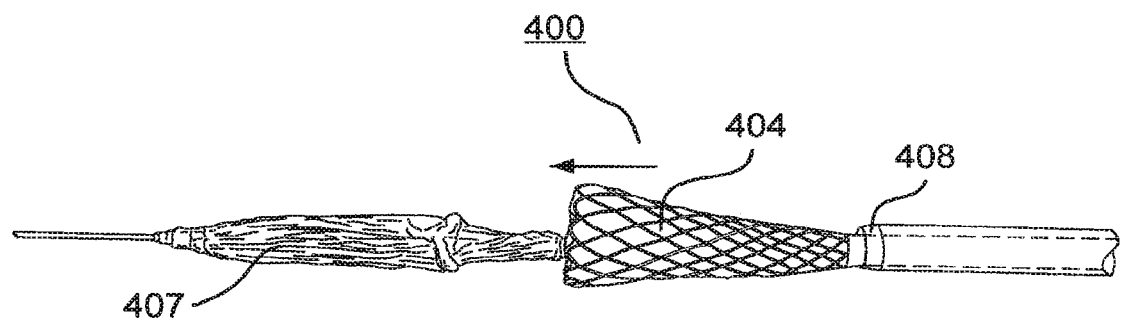
Figure 4C:
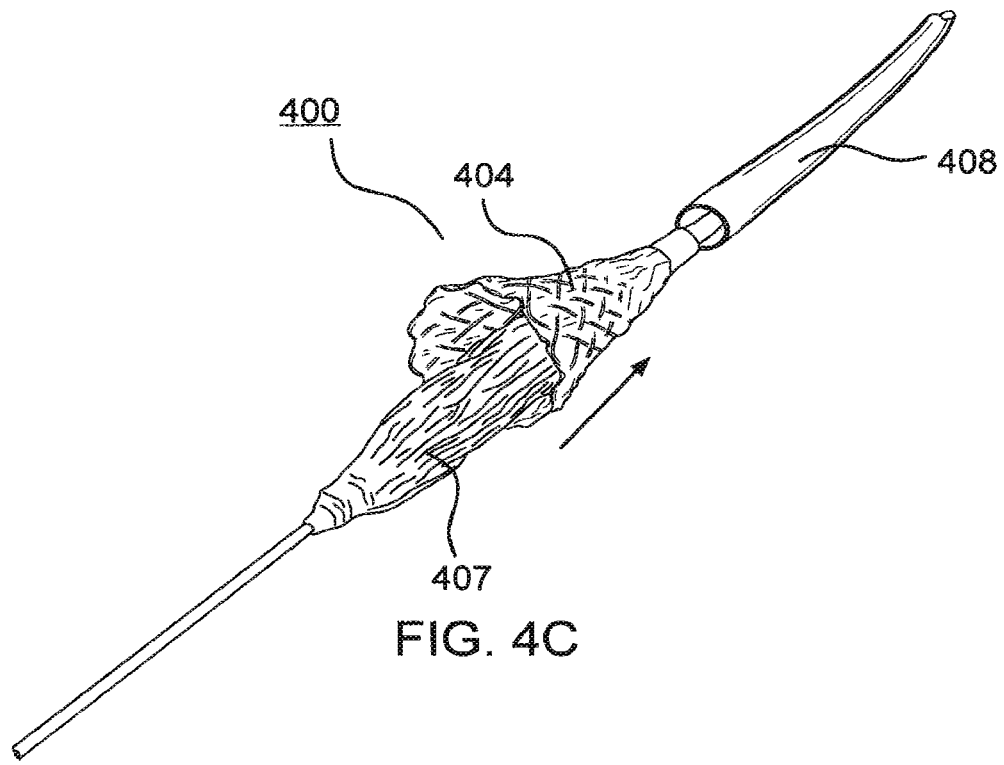
Figure 4D:
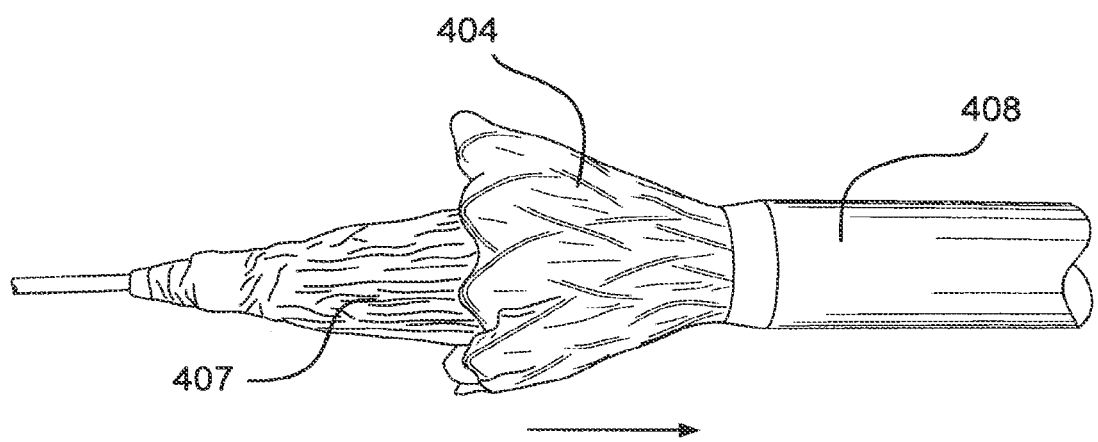
Figure 4E:
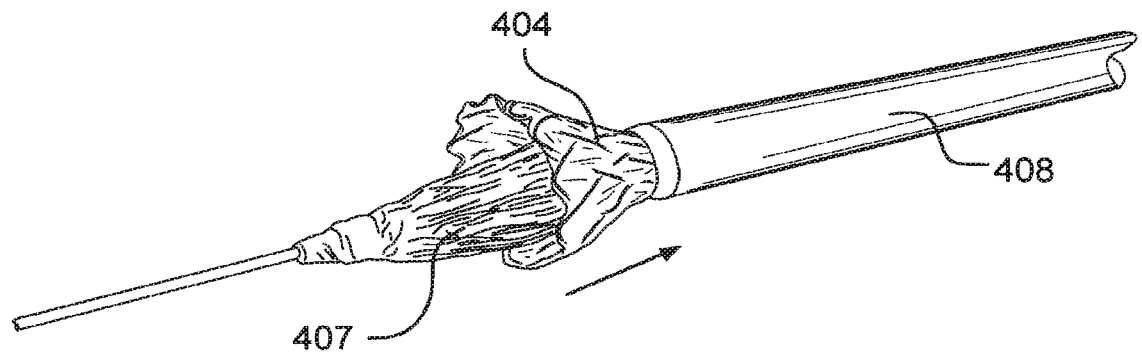
Figure 4F:
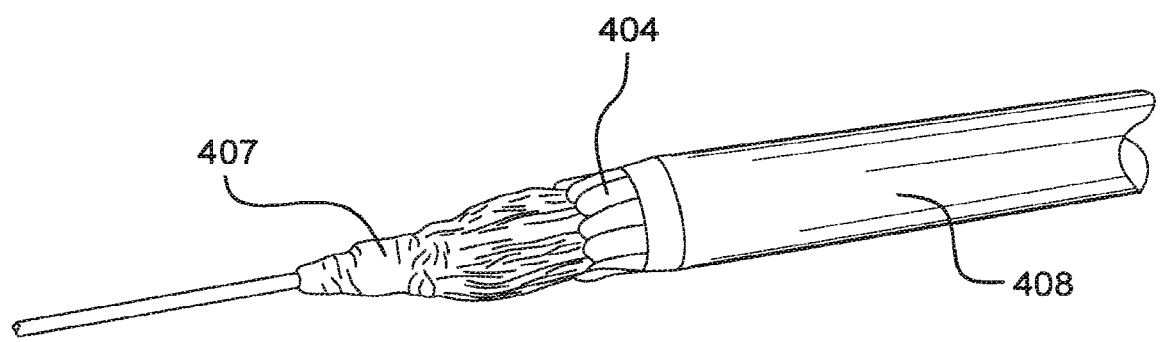
Figure 4G:
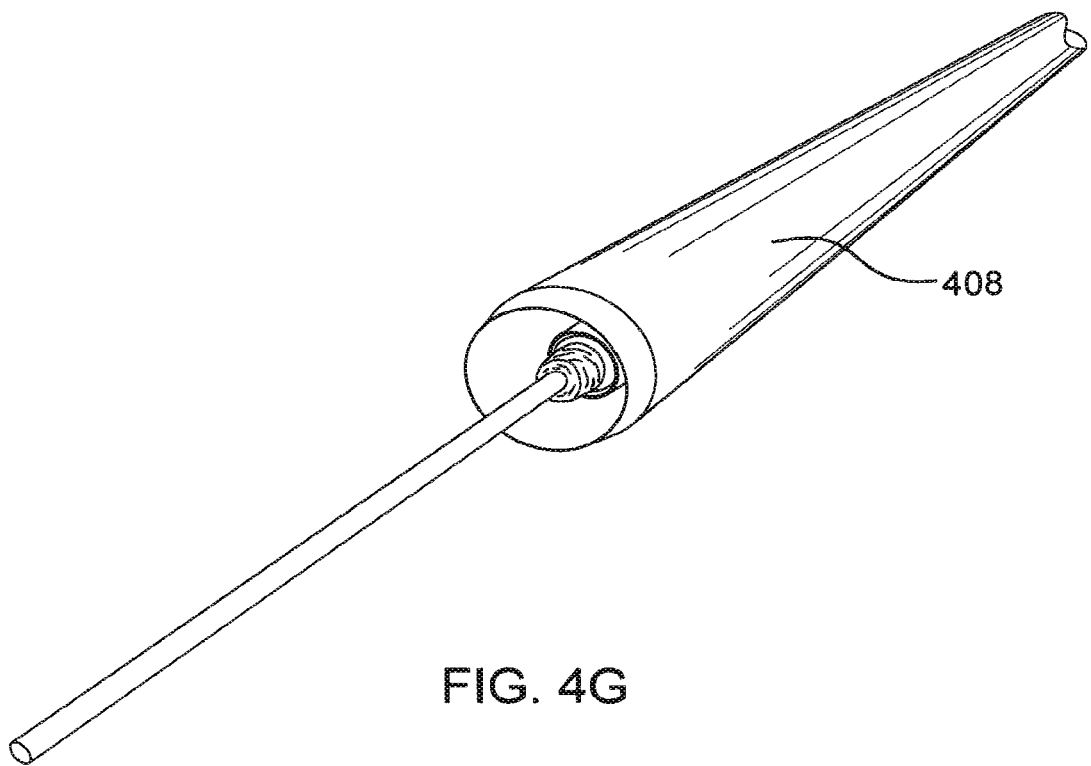

Methods of using devices in accordance with the present disclosure are also disclosed herein. For example, FIGS. 4A-4G progressively illustrate a method for retrieving a failed endoluminal balloon using an embodiment of the retrieval device of FIG. 1. At the outset, FIG. 4A illustrates an endoluminal balloon 407 that failed to refold upon removal though an introducer 408. As shown in FIG. 4B, a retrieval device 400 is coupled with the balloon catheter as a system. The collapsible retriever 404 of retrieval device 400 is then positioned past the distal end of introducer 408. Next, as illustrated in FIG. 4C, endoluminal balloon 407 is pulled into and enveloped or engulfed by collapsible retriever 404. In this regard, a cumulative force is exerted and distributed substantially evenly about endoluminal balloon 407. Finally, as shown in FIGS. 4D-4G, as the system is withdrawn through introducer 408, collapsible retriever 404 packs endoluminal balloon 407 and reduces its extraction french size.

Figure 5A:
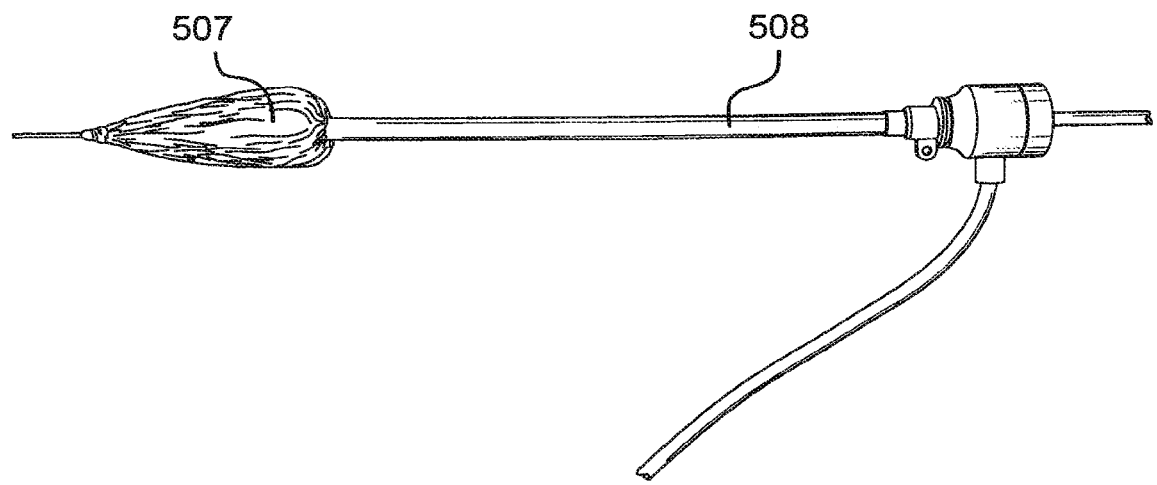
FIGS. 5A-5G progressively illustrate a method for retrieving a failed endoluminal balloon using an embodiment of the retrieval device of FIGS. 2A-2B.
Figure 5B:
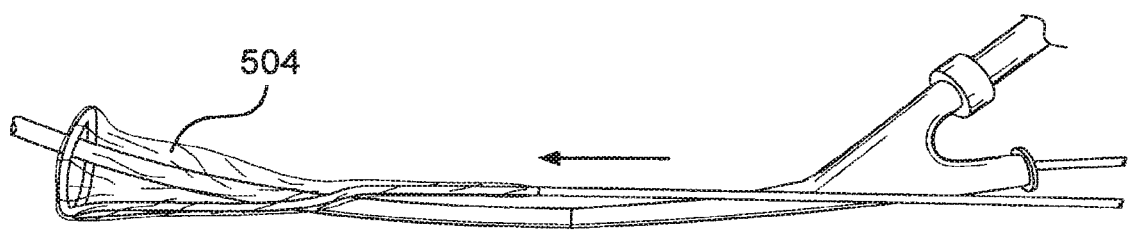
Figure 5C:
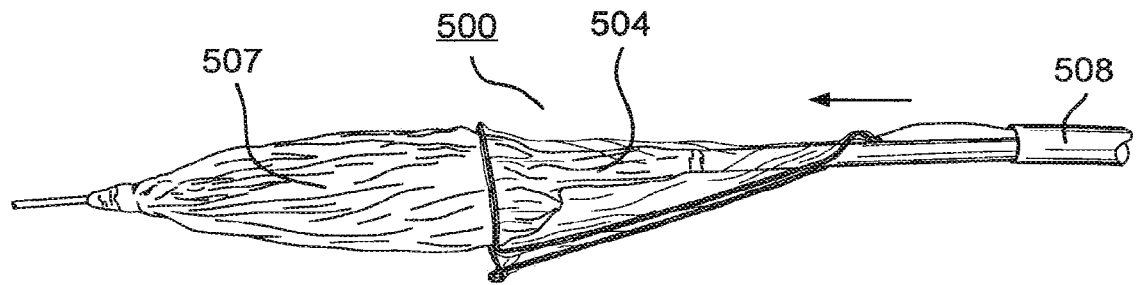
Figure 5D:
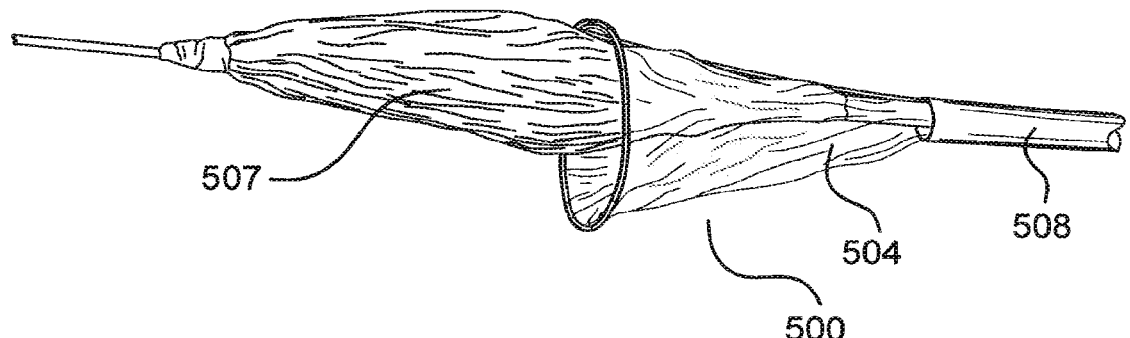
Figure 5E:
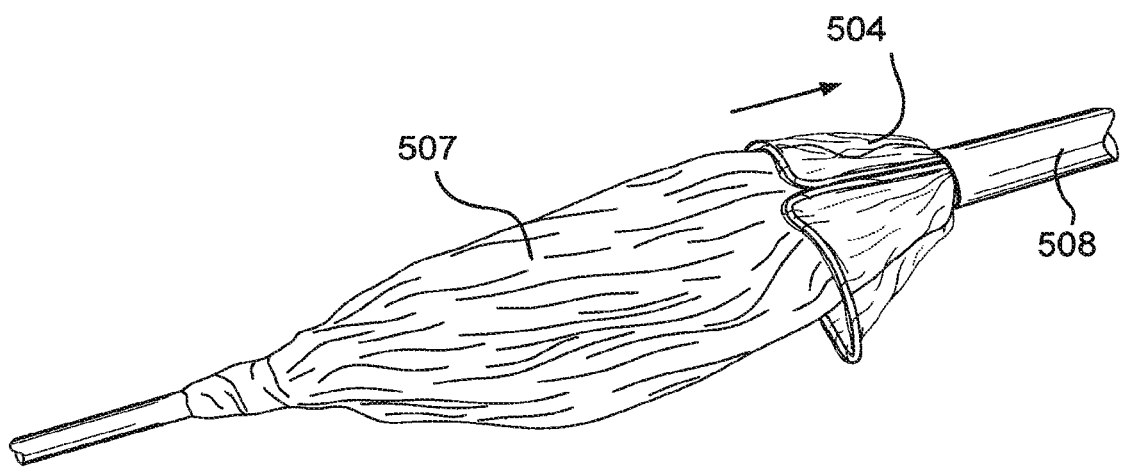
Figure 5F:
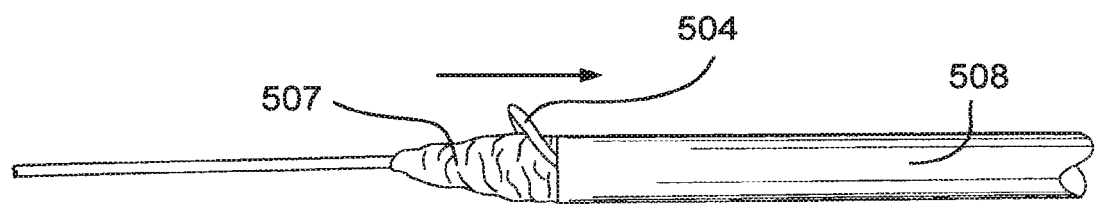
Figure 5G:
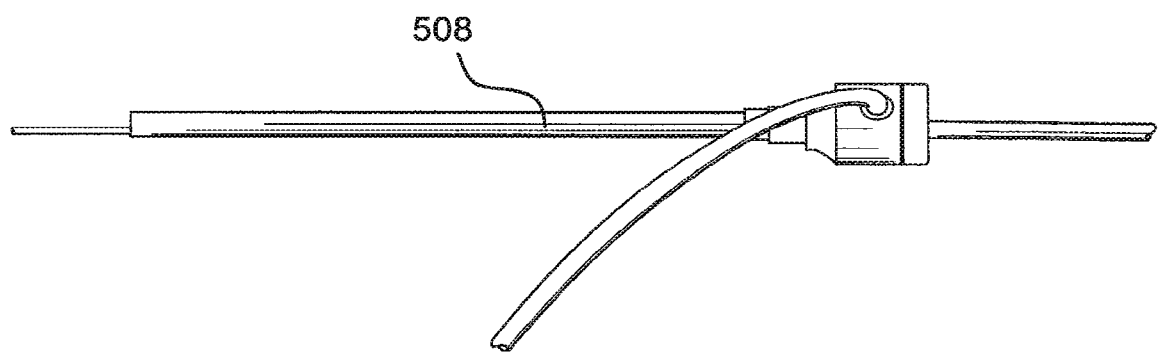

Similarly, FIGS. 5A-5G illustrate a method for retrieving a failed endoluminal balloon using an embodiment of the retrieval device of FIGS. 2A-2B. At the outset, FIG. 5A illustrates an endoluminal balloon 507 that failed to repack during removal though an introducer sheath 508. As shown in FIG. 5B, a retrieval device 500 is placed over the balloon catheter and delivered through introducer sheath 508 to the site. The collapsible retriever 504 of retrieval device 500 advances past the distal end of coaxial element, e.g., an introducer sheath 508. Next, as illustrated in FIG. 5C, endoluminal balloon 507 is pulled into and enveloped or engulfed by collapsible retriever 504. In this regard, a cumulative force is exerted and distributed substantially evenly about endoluminal balloon 507. Finally, as shown in FIGS. 5D-5G, as the system is withdrawn through introducer sheath 508, collapsible retriever 504 packs endoluminal balloon 507 and reduces its extraction french size.

In various embodiments, a method of retrieval can comprise placing collapsible retriever 504 about an delivery element, such as a balloon catheter; advancing collapsible retriever 504 into a position, wherein the position is beyond the distal end of a coaxial delivery element, such as an outer catheter or introducer sheath 508; retracting at least a portion of an endoluminal device, e.g., endoluminal balloon 507, into the lumen of collapsible retriever 504; retracting collapsible retriever 504 and the endoluminal device into a lumen of the coaxial delivery element. Upon retraction, collapsible retriever 504 will extend in a proximal to distal direction and collapse about at least a portion of the endoluminal device.

Figure 6B:
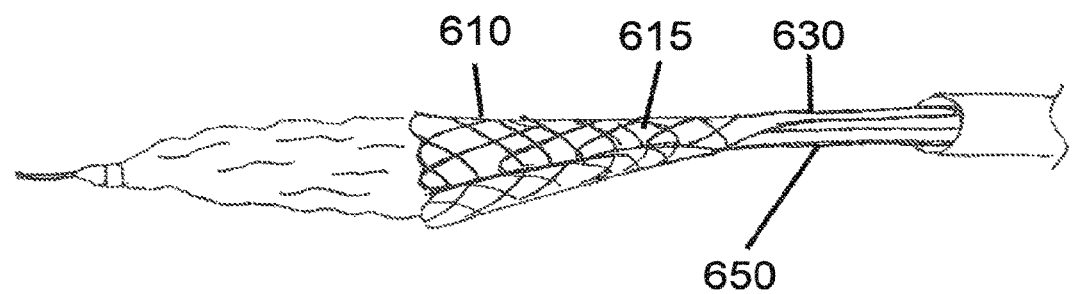
Figure 6C:
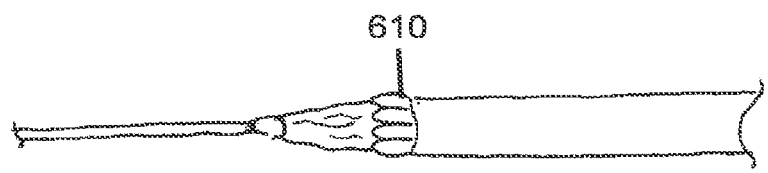

In various embodiments, placing collapsible retriever 504 about the delivery element can comprise side mounting the delivery element. As described previously, collapsible retriever 504 can be configured to have a discontinuous wall section along its length that allows collapsible retriever 504 to be placed on a delivery element from the side, thus avoiding the need to cut the delivery element at the hub in order to place the collapsible retriever about the delivery element. Accordingly, in such embodiments, a negative pressure within a balloon can be maintained during retraction In another embodiment, with reference to FIGS. 6A-6C a method of using can comprise placing a retrieval device 600 as described herein in an uncoupled configuration, about a section of a delivery element 650, collapsible retriever 610 having a proximal end and a distal end and a first side edge opposite from a second side edge. The first side edge is then coupled to the second side edge to form a retriever 610 in a coupled configuration and defining tapered lumen. The retrieval device 600 can then be advanced in the coupled configuration in a distal direction through the coaxial delivery element and toward the object to be retrieved. The retriever 610 can be fixedly/securely coupled to an elongate member 630. In an embodiment, as shown, collapsible retriever can comprise a lattice element 615.

Once the object is reached, collapsible retriever 610 in the coupled configuration is placed at least partially about the object. In various embodiments, the distal end of retriever 610 is pressed against the object causing the distal end of retriever 610 to radially expand. In an embodiment, the coupled retriever can then be advanced along the length and then retracted along with the object into the lumen of a coaxial element.

Placing collapsible retriever about the delivery element can comprise side mounting the delivery element. Capability to side-mount allows collapsible retriever to be placed on a delivery element from the side, thus avoiding the need to cut the delivery element at the hub in order to place the collapsible retriever about the delivery element. Accordingly, in such embodiments, a negative pressure within a balloon can be maintained during retraction.

Figure 7A:
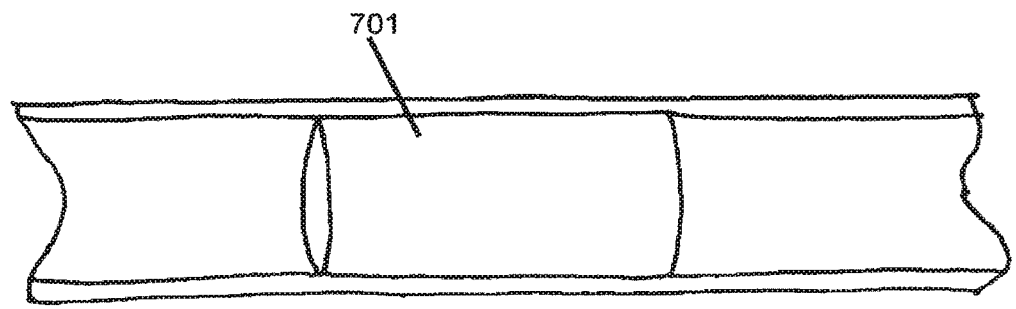
FIGS. 7A to 7E illustrate a method for retrieving a failed endoluminal device using an embodiment as shown in FIGS. 3A to 3C.
Figure 7B:
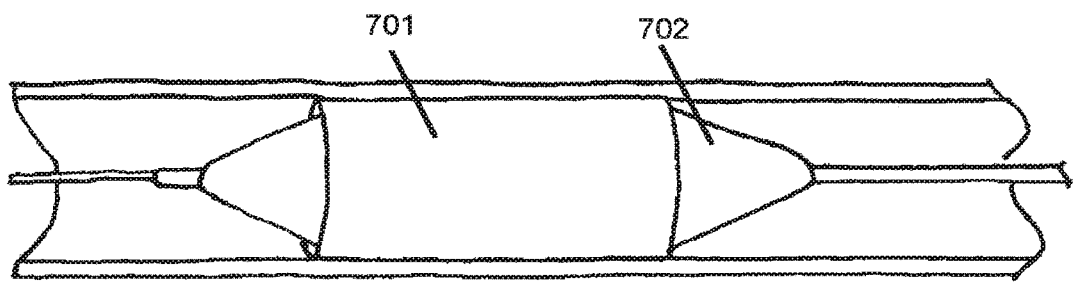
Figure 7C:
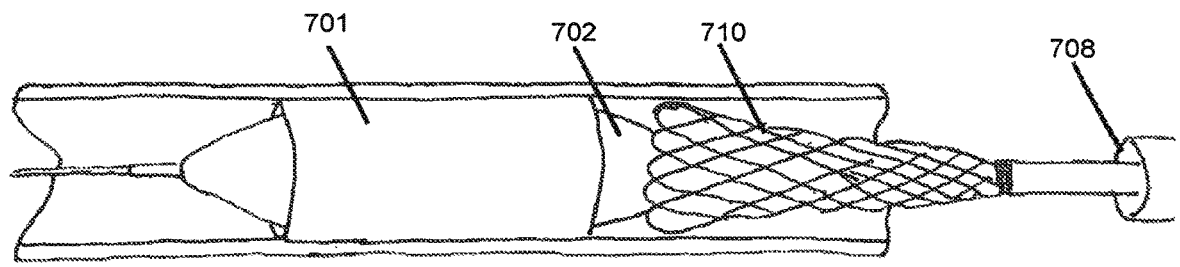
Figure 7D:
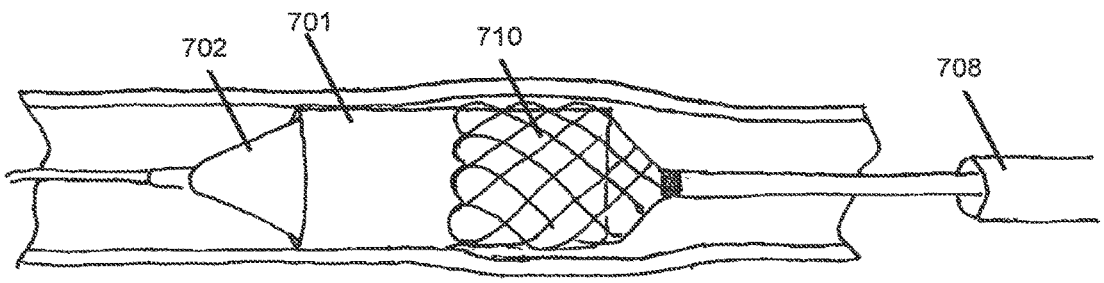
Figure 7E:
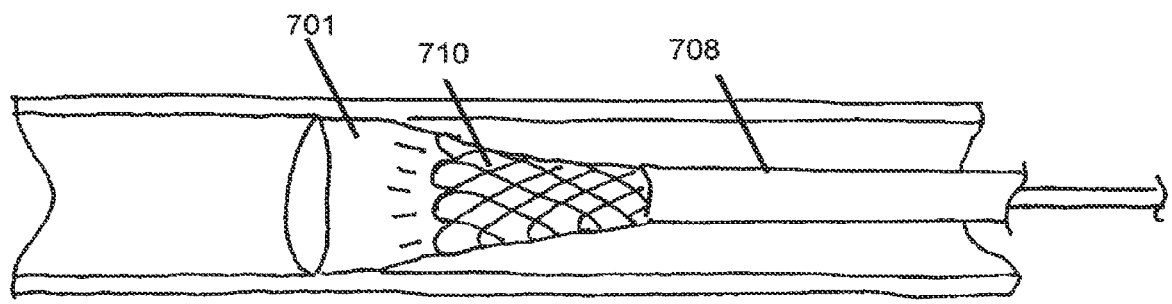

In an embodiment, with reference to FIG. 7A-7D, methods of using as described herein can further comprise the step of securing or holding an object in position with a securing device. A securing device can comprise an expandable member that can provide a counterforce upon the object as the collapsible retriever is advancing at least partially about the object. In an embodiment, the expandable member can be a balloon. As illustrated in FIG. 7A, an object 701 to be retrieved can be located in a vessel. As illustrated in FIG. 7B, the securing device 702 can be positioned and deployed at a location on the distal side of the object 701, opposite the side from which the collapsible retriever 710 is advanced. As illustrated in FIGS. 7C to 7D, once the securing device 702 is deployed, the collapsible retriever 710 can then advance toward the object 701 and be pressed against the object 701 to envelop at least partially, while mitigating the risk of moving the object 701 with the aid of the securing device 702. As described supra, in an embodiment, the distal mouth of the collapsible retriever 710 can be configured to radially expand when pressed against the object 701. As illustrated in FIG. 7E, a coaxial element 708 can be advanced over both the object 701 and the collapsible retriever 710.

Methods of making a retrieval device are also provided. In an embodiment, a collapsible retriever comprising a nitinol lattice and an ePTFE membrane is formed by sandwiching a braided nitinol tube between ePTFE films with fluorinated ethylene propylene (FEP) lining the ePTFE films on the side in contact with the nitinol braid. The frame is first formed from wrapping a nitinol wire around a mandrel. An appropriately shaped conical mandrel is used. The collapsible retriever device is then heat set while on the mandrel for approximately 10-20 minutes at approximately 450° C. The resulting retriever can then be covered, lined, or covered and lined as necessary. For example, an FEP powder-coat can be applied to the member and then ePTFE tape can be wrapped in a helical pattern that matches the braid angle. The collapsible retriever device is then heat set while on the mandrel for approximately 12-20 minutes at approximately 320° C. The small diameter portion of the collapsible retriever is coupled to an appropriately sized elongate element using a wrap or biocompatible adhesive.

In another embodiment, a collapsible retriever comprising a nitinol frame and an ePTFE membrane is formed by sandwiching a nitinol wire between ePTFE films with fluorinated ethylene propylene (FEP) lining the ePTFE films on the side in contact with the nitinol wire. The frame is first formed from wrapping a nitinol wire around an appropriately jigged conical mandrel. The frame is then transferred to a smooth, conical mandrel and then coated with FEP powder and covered with ePTFE film imbibed with an elastomer. The shaped frame is then heat set while on the mandrel for approximately 10-20 minutes at approximately 320° C.

The collapsible retriever can allow perfusion and serve to minimize or eliminate the "vapor lock" phenomena by allowing blood into the workspace, which may enable an easier retrieval of an object. For example, in the case of thrombus, a perforated retriever can facilitate the release of fluid and a reduction in the volume of the thrombus as the thrombus is being pulled into the coaxial element and thereby compressed. A perfusable retriever can be made by laser perforating one layer of a thin, polytetrafluoroethylene (PTFE) membrane using a 10-watt $CO_2$ laser. The membrane thickness can measure about 0.0002" (0.005 mm) and have tensile strengths of about 49,000 psi (about 340 MPa) in a first direction and of about 17,000 psi (about 120 MPa) in a second direction (perpendicular to the first direction). The tensile measurements can be performed at 200 mm/min. load rate with a 1" (2.5 cm) jaw spacing. The membrane can have a density of about 2.14 g/cm.sup.3. The laser power and shutter time parameters can be adjusted to allow the laser to consistently create uniform 0.004" (0.1 mm) diameter holes in the membrane. The hole pattern geometry can be then adjusted to create a pattern with uniform hole size, uniform hole spacing, and uniform strength throughout the pattern. This perforated pattern can be then folded on itself and heat-sealed using a local heat source (Weber soldering iron, EC2002M, (available through McMaster Carr, Santa Fe Springs, Calif.)) into a pattern which will result in a conical shape. The conical flat pattern can then be trimmed with scissors, inverted, and mounted upon the FEP powder coated NiTi frame and attached though the application of localized heat (the heat causing the FEP coating on the frame to re-melt and flow onto the surface of the filter sack thus providing a biocompatable thermoplastic adhesive).

A method of making a retrieval device as shown in FIG. 3A to 3C is illustrated in FIGS. 8A to 8D. In an embodiment, a method of making can comprise providing a generally flattened frustoconical member 801 having a first side edge 814 and a second side edge 812. The flattened frustoconical member 801 can be a latticed construction. The flattened frustoconical member 801 can be formed into a generally conical form 810 wherein the first side edge 814 and second side edge 812 are adjacent and interlockable. A first side edge 814 can also be inverted to form a channel and a second side edge can be shaped and reinforced to securely engage with the channel.

In an embodiment, to fabricate an interlocking conical collapsible retriever, a large diameter, self-expanding metallic braid is acquired. (for instance, having a 75 mm diameter). The braided tube will be flattened and a portion will be inverted. The flattened member can be heat set at 450° C. for approximately 10 minutes and then quenched in a water bath. The flattened member can then be formed into a tube, and the sides can be interlocked. The tube is now approximately 37 mm in diameter. To form a conical shape, one end of the tube can be necked down to a desired diameter, e.g., a dimension amenable to attachment to an elongate member. Once the desired shape and dimension are obtained, the member can be heat set at 470° C. for approximately 12 minutes and then quenched in a water bath. In this manner, a double-walled, self-expanding collapsible retriever in a frustoconical shape having interlocking edges will be formed. The resulting retriever can then be covered, lined, or covered and lined as necessary. For example, an FEP powder-coat can be applied to the member and then ePTFE tape can be wrapped in a helical pattern that matches the braid angle. After application and adherence, slit the ePTFE covering and/or lining at the interlock seam to allow "side-mounting."

It will be apparent to those skilled in the art that various modifications and variations can be made in the present disclosure without departing from the spirit or scope of the disclosure. For example, while embodiments of the present disclosure have been described primarily with reference to endoluminal balloons, embodiments are scalable and applications for retrieval of various endoluminal devices are contemplated herein. In addition, the various described elements can be combined in any number of combinations not limited to those shown in the figures. Likewise, the described embodiments can be used in connection with not just humans, but also various organisms having mammalian anatomies. Thus, it is intended that the described embodiments cover the modifications and variations of this disclosure provided they come within the scope of the appended claims and their equivalents.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

What is claimed is:

1. A retrieval device to be side-mounted on an elongate member, the device comprising:
   a retriever having a proximal end and a distal end and at least partially defining a tapered lumen therethrough; and
   a circumferential member positioned at the distal end of the retriever and operable to radially compress the distal end of the retriever,
   wherein the retriever comprises an interlocking section extending along at least a portion of the retriever between the proximal end to the distal end,
   wherein the interlocking section comprises a first side edge and a second side edge, and wherein each side edge has a structural feature that facilitates at least partially coupling the first side edge to the second side edge.

2. The device of claim 1, wherein the interlocking section comprises a tongue and groove interface.

3. The device of claim 1, wherein the retriever comprises a wall having an interior face and an exterior face, the interior face at least partially defining the tapered lumen.

4. The device of claim 3, wherein the retriever has a cross-sectional area at the distal end and the cross-sectional area increases upon application of a compressive force applied along an axis formed between the proximal end and the distal end.

5. The device of claim 4, wherein the wall comprises a lattice element defining the tapered lumen and configured to radially expand upon application of a compressive force applied along the axis formed between the proximal end and the distal end.

6. The device of claim 4, wherein the wall comprises a film material, the film material overlaying at least a portion of the lattice element.

7. The device of claim 3, wherein the wall comprises at least two layers.

8. The device of claim 3, wherein the exterior face has a low friction surface relative to a surface of the interior face.

9. The device of claim 1, further comprising an elongate element having a proximal end and a distal end and a longitudinal axis, wherein the distal end of the elongate element is coupled to the proximal end of the retriever.

10. A retrieval device to be side mounted on an elongate member, the device comprising:
a collapsible retriever having a proximal end and a distal end and a first side edge opposite from a second side edge along at least a portion of the collapsible retriever between the proximal end and the distal end, and
a circumferential member positioned at the distal end of the collapsible retriever and operable to radially compress the distal end of the collapsible retriever,
wherein the collapsible retriever has a coupled configuration and an uncoupled configuration, wherein the first edge couples to the second edge to form the coupled configuration, and wherein the collapsible retriever, in the coupled configuration, defines a tapered lumen.

11. The device of claim 10, wherein the collapsible retriever comprises a wall having an interior face and an exterior face, the interior face at least partially defining the tapered lumen.

12. The device of claim 11, wherein the collapsible retriever has a cross-sectional area at the distal end and the cross-sectional area increases upon application of a compressive force applied along an axis formed between the proximal end and the distal end.

13. The device of claim 12, wherein the wall comprises a lattice element defining the tapered lumen and configured to radially expand upon application of a compressive force applied along the axis formed between the proximal end and the distal end.

14. The device of claim 13, wherein the wall comprises a film material, the film material overlaying at least a portion of the lattice element.

15. The device of claim 11, wherein the wall comprises at least two layers.

16. The device of claim 11, wherein the exterior face has a low friction surface relative to a surface of the interior face.

17. The device of claim 10, further comprising an elongate element having a proximal end and a distal end and a longitudinal axis, wherein the distal end is coupled to the proximal end of the collapsible retriever.

18. The device of claim 10, wherein the first side edge couples to the second side edge to form an interlocking section.

19. The device of claim 18, wherein the interlocking section comprises a tongue and groove interface.

20. The device of claim 10, wherein the collapsible retriever comprises a circumferential member coupled to an axial member, wherein the circumferential member compresses the collapsible retriever upon rotation or axial movement of the axial member.

21. The device of claim 1, further comprising an axial member operable to be rotated to cause radial compression of the circumferential member.

22. The device of claim 1, wherein the circumferential member is a filament.

23. The device of claim 5, wherein the circumferential member is woven through the lattice element.

24. The device of claim 1, wherein the circumferential member is operable to be tensioned to radially compress the retriever.

* * * * *